United States Patent [19]

Stine et al.

[11] 4,028,430
[45] June 7, 1977

[54] SIMULATED MOVING BED REACTION PROCESS

[75] Inventors: Laurence O. Stine, Western Springs; Dennis J. Ward, South Barrington, both of Ill.

[73] Assignee: Universal Oil Products Company, Des Plaines, Ill.

[22] Filed: June 16, 1975

[21] Appl. No.: 587,468

[52] U.S. Cl. .................. 260/683.43; 260/671 R
[51] Int. Cl.² .................................. C07C 3/50
[58] Field of Search .............. 208/146; 260/671 R, 260/683.43

[56] References Cited

UNITED STATES PATENTS

| 2,541,044 | 2/1951 | Daugherty | 260/671 |
| 2,635,988 | 4/1953 | Crowley | 208/146 |
| 3,377,400 | 4/1968 | Wise | 260/671 |

*Primary Examiner*—Delbert E. Gantz
*Assistant Examiner*—Charles Spresser
*Attorney, Agent, or Firm*—James R. Hoatson, Jr.; Thomas K. McBride; William H. Page, II

[57] ABSTRACT

A continuous catalytic reaction and catalyst reactivation process is carried out using a simulated moving catalyst bed to effect simultaneously in different zones of a multi-zone fixed catalyst bed an alkylation reaction of olefin and isoparaffin reactants and a reactivation of catalyst.

10 Claims, 1 Drawing Figure

SIMULATED MOVING BED REACTION PROCESS

BACKGROUND OF THE INVENTION

This invention relates in general to a continuous catalytic reaction process utilizing a simulated moving catalyst bed to effect simultaneously in different zones of a catalyst bed containing at least three zones, a reaction of reactants and a reactivation of a catalyst in the catalyst bed, and more specifically, this invention relates to an application of a simulated moving catalyst bed to an alkylation reaction process.

One of the problems in carrying out a catalytic reaction is that of catalyst deactivation. In essentially all catalytic reactions, over a period of time the catalyst will lose part of its activity. It is common practice to discard or regenerate a catalyst when its activity is sufficiently low to cause inefficiency or unprofitability, at which point the catalyst is considered "spent". Various schemes are used to reactivate or regenerate a catalyst depending on catalyst characteristics, the process scheme and economic considerations. Generally, the operation to regenerate a catalyst is considered unprofitable, although at least in certain processes, some, and even a great benefit is directly derived from a catalyst regeneration operation. When an operating plant must be taken out of operation for the purpose of conduction a regeneration of a catalyst, and production time is lost, the economic liability is especially great. Typical examples of processes which require shutdown of normal operations to regenerate catalyst include naphtha reforming a high octane gasoline, hydrocracking, hydrodesulfurization, and di-olefin saturation, to name but a few, and in these processes, it is common for a plate to be shutdown about 2 to 10 percent of a calendar year for the purpose of catalyst regeneration. In other processes, the catalyst deactivation rate is so great that reactors must be installed in duplicate to allow normal operation in one, while regeneration or replacement of the catalyst in the stand-by reactor takes plate. An example of such a process is a process for dehydrogenation of paraffins to olefins, but the technique of providing stand-by reactors or contactors is more common for simple operations like air drying. Another regeneration scheme is the recent development of continuous regeneration of a small portion of a catalyst bed by continously removing a catalyst portion from the bed, regenerating it is continuous facilities external to the catalyst bed, and continuously returning regenerated catalyst to the catalyst bed. This method of catalyst regeneration has been successfully applied to a reforming process in which naphtha is upgraded to high octane gasoline. Still another regeneration technique is that commonly employed in fluid catalytic cracking units, wherein the entire catalyst bed is continuously moving between a reaction zone and a regeneration zone during normal operation.

Each of the above described regeneration schemes has benefits and liabilities which make the scheme applicable to a given process and not another. The continuous schemes are becoming more desirable as processing severity increases, resulting in more rapid catalyst deactivation. From a historical viewpoint, it is seen that economics favor increasing reaction severity for many catalytic reactions, resulting in higher product yields and higher product quality and a greater catalyst deactivation rate. While catalyst development has resulted in more active, more stable catalysts, emphasis is being placed on maintaining essentially fresh catalyst activity throughout the duration of a catalyst run. In many processes, the increased value of a higher product yield or higher product quality throughout a catalyst run is greater than the increased cost of maintaining a higher catalyst activity, either through more expensive, more stable catalysts or though continuous regeneration schemes.

While the new reaction/regeneration scheme may be applicable to many present processes, such a new scheme may also be applied to certain catalyst preparations which cannot now be economically utilized due to a combination of high catalyst deactivation rate and an unsatisfactory regeneration scheme.

SUMMARY OF THE INVENTION

Accordingly it is an object of this invention to provide a processing scheme which will result in higher product yields and higher product quality in a catalytic process. Another object is to allow use of more active, less stable catalysts to achieve higher product yields and higher product quality in a catalytic process. A specific object of this invention is to provide a combination catalytic reaction-catalyst reactivation process which will allow simultaneous, continuous reactivation of a catalyst in one zone while the catalyst bed is in normal operation in another zone of a fixed catalyst bed. A further specific object is to apply the continuous catalytic reaction/catalyst reactivation scheme of the present invention to an alkylation reaction process.

In an embodiment, this invention relates to a continuous fixed bed catalytic reaction and catalyst reactivation process comprising the steps of: (a) providing a fixed bed of solid catalyst containing four zones having a fluid flow connecting path between said zones to interconnect said zones; (b) arranging said zones in a series and providing fluid flow connecting means between the last zone and the first zone of the series to provide a directional circular flow path through said zones; (c) providing a point between each two successive zones for introducing an inlet stream or withdrawing a product stream; (d) introducing a reactivation stream at a first point located between two successive zones (zone II and zone III) to effect catalyst reactivation; (e) simultaneously withdrawing a first product stream from a second point located between said zone III and the next successive zone in the direction of flow (zone IV); (f) simultaneously introducing a reactants stream into said fixed bed of catalyst at a third point located between said zone IV and the next successive zone in the direction of flow (zone I) to effect a reaction, a result of which is deactivation of said catalyst; (g) simultaneously withdrawing a second product stream from a fourth point located between said zone I and the next successive zone in the directin of flow (zone II); and, (h) periodically advancing downstream the points of charging said reactants stream and said reactivation stream, and the points of withdrawal of said product streams to the next successive points for introducing an inlet stream or withdrawing an outlet stream.

In another embodiment, the present invention relates to a continuous fixed bed catalytic reaction and catalyst reactivation process comprising the steps of: (a) providing a fixed bed of solid catalyst containing three zones having a fluid flow connecting path between said zones to interconnect said zones; (b) arranging said zones in a series and providing fluid flow connecting means between the last zone and the first zone of the series to provide a directional circular flow path through said zones; (c) providing a point between each two successive zones for introducing an inlet stream or withdrawing a product stream; (d) introducing a reactivation stream at a first point located between two successive zones to effect catalyst reactivation; (e) simultaneously withdrawing a first product stream from a second point located between another two successive zones; (f) simultaneously introducing a reactants stream into said fixed bed of catalyst at a third point located between the remaining two successive zones to effect a reaction, a result of which is deactivation of said catalyst; and (g) periodically advancing downstream the points of charging and reactants stream and said reactivation stream, and the point of withdrawal of said product stream to the next successive points for introducing an inlet stream or withdrawing an outlet stream.

In a specific embodiment, the present embodiment relates to a continuous fixed bed catalytic alkylation reaction and catalyst reactivation process comprising the steps of: (a) providing a fixed bed of solid catalyst containing four zones having a fluid flow connecting path between said zones to interconnect said zones; (b) arranging said zones in a series and providing fluid flow connecting means between the last zone and the first zone of the series to provide a directional circular flow path through said zones; (c) providing a path between each two successive zones for introducing an inlet stream or withdrawing a product stream; (d) introducing a reactivation stream including alkylatable hydrocarbon at a first point located between two successive zones (zone II and zone III) to effect catalyst reactivation and to provide alkylatable hydrocarbon as a continuous component throughout said fixed bed of solid catalyst; (e) simultaneously withdrawing a first product stream from a second point located between said zone III and the next successive zone in the direction of flow (zone IV); (f) simultaneously introducing a reactants stream including an olefin-acting reactant into said fixed bed of catalyst at a third point located between said zone IV and the next successive zone in the direction of flow (zone I) to effect an alkylation reaction, a result of which is deactivation of said catalyst; (g) simultaneously withdrawing a second product stream from a fourth point located between said zone I and the next successive zone in the direction of flow (zone II); and, (h) periodically advancing downstream the points of charging said reactants stream and said reactivation stream, and the points of withdrawal of said product streams to the next successive points for introducing an inlet stream or withdrawing an outlet stream.

In another specific embodiment, the present invention relates to a continuous fixed bed catalytic alkylation reaction and catalyst reactivation process comprising the steps of: (a) providing a fixed bed of solid catalyst containing three zones having a fluid flow connecting path between said zones to interconnect said zones; (b) arranging said zones in a series and providing fluid flow connecting means between the last zone and the first zone of the series to provide a directional circular flow path through said zones; (c) providing a point between each two successive zones for introducing an inlet stream or withdrawing a product stream; (d) introducing a reactivation stream including alkylatable hydrocarbon at a first point located between two successive zones to effect catalyst reactivation and to provide alkylatable hydrocarbon as a continuous component throughout said fixed bed of solid catalyst; (e) simultaneously withdrawing a first product stream from a second point located between another two successive zones; (f) simultaneously introducing a reactants stream including an olefin-acting reactant into said fixed bed of catalyst at a third point located between the remaining two successive zones to effect an alkylation reaction, a result of which is deactivation of said catalyst; and, (g) periodically advancing downstream the points of charging said reactants steam and said reactivation stream, and the point of withdrawal of said product stream to the next successive points for introducing an inlet stream or withdrawing an outlet stream.

DETAILED DESCRIPTION OF THE INVENTION

The present process is applicable generally to catalytic reaction processes in which a solid catalyst employed is deactivated and can be reactivated by contacting it with a reactivation medium. No limitation of the invention process is intended in regard to reactants, catalyst, or reaction exept that it is not applicable to non-catalytic processes or to processes in which a solid catalyst employed cannot be reactivated.

In this description, the word "reactivation" when applied to a catalyst will indicate removal from the catalyst of an impurity or matter which deactivates the catalyst. This may be in the form of a regeneration wherein coke is burned off a catalyst with oxygen; a reactivation wherein a reactivation medium reacts with an impurity deposited on a catalyst, e.g., carbon monoxide reacting with nickel to remove the nickel deposited on the catalyst; a reactivation wherein a depleted material is added to a catalyst to enhance the activity of the catalyst, e.g., chloride or water addition to a reforming type catalyst, a reactivation resulting from sweeping a deactivation medium off the surface of or out of the pores of a catalyst by a suitable reactivation medium, e.g., flushing tars, polymers, high molecular weight hydrocarbons, residue, or particulate matter out of a catalyst with a suitable dissolving or flushing agent; a reactivation wherein an adsorbed unsaturated species is hydrogenated to a less tightly adsorbed species; or any other form of reactivation involving contact of a reactivation medium with a catalyst. The present process is also applicable to a catalyst which does not deactivate in the sense that the catalyst loses activity, but rather the catalyst particles and the catalyst bed become "plugged" with an undesirable material which causes pressure drop in the catalyst bed. In this case a reactivation medium must be available to remove the undesirable material, to keep the catalyst active in the sense that reactants can contact the catalyst, and to keep pressure drop from building across the catalyst bed.

No limitation is herein intended in regard to reactants and catalytic reactions employed in the present process. The invention is applicable to processes such as alkylation, diolefin saturation, hydrocracking, catalytic cracking, desulfurization, dehydrogenation, polymerization, isomerization, reforming, and flue gas desulfurization, to name but a few, without restricting the inventive concept of these processes. The common basis for applying the present invention to the above listed processes lies in their use of a solid catalyst, although different in each process, which can be reactivated when the catalyst becomes deactivated.

No limitation is herein intended in respect to the catalyst employed in the present invention except that it cannot be fluid. In general, the catalyst is a solid particle, the shape of it being unimportant in the present invention. Besides having catalytic properties, the catalyst may exhibit adsorbent properties and allow some degree of separation of reactants, products, and reactivation media in accordance with the simulated moving bed scheme of the present inventive process. The catalyst may also take solid forms other than particles. Especially preferred for use in the present invention because of their high activity and low stability are crystalline zeolitic molecular sieves, either prepared singly or in combination with one or more metal activators. Preparation of suitable zeolitic catalysts is well known in the prior art and can be found in U.S. Pat. Nos. 2,882,244, 3,130,007, 3,216,789 3,375,064, and others. Other suitable catalysts include Friedel-Crafts metal halides such as aluminum chloride on a support such as alumina; solid phosphoric acid; boron trifluoride-modified refractory inorganic oxide; halogenated alumina composited with metal activators such as platinum or palladium alone or in combination with other metal activators; mordenite composited with a metal activator such as platinum or palladium alone or in combination with other metal activators; alumina composited with metal activators of cobalt, nickel, and molybdenum; magnesia composited with ferric oxide and potassium oxide; chromia-alumina modified with alkali, zinc compounds, or beryllia; aluminasilica composited with metal activators of cobalt, nickel, and molybdenum; etc.

Figure 1:
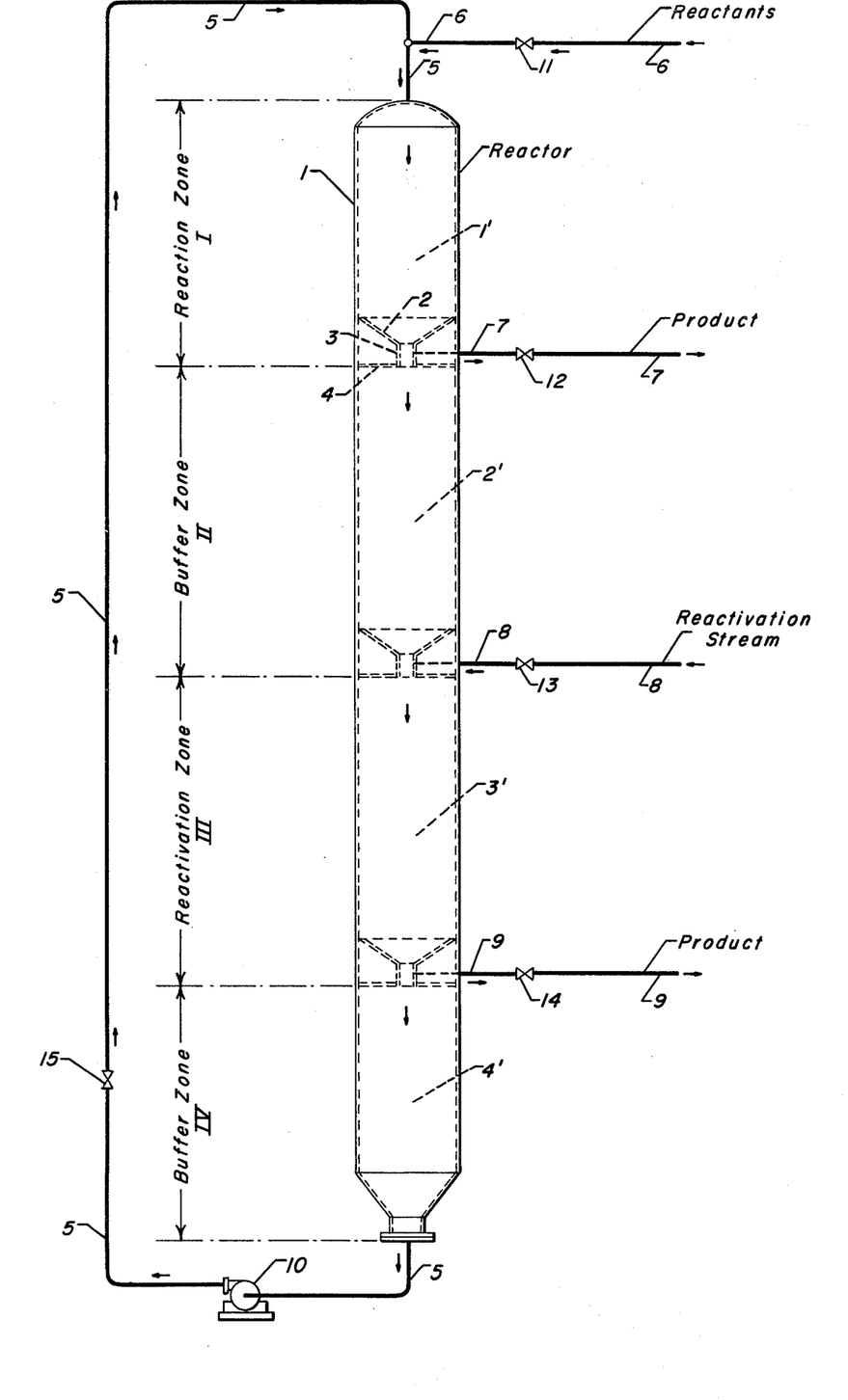

An understanding of this invention may be aided by reference to the accompanying drawing which represents a schematic flow diagram of an embodiment of the inventive process. The present invention concerns application of a simulated moving bed technique described in U.S. Pat. No. 2,985,589 and others to a catalytic process in which a catalytic reaction and a reactivation of the catalyst employed take place in different zones of a catalyst bed. Referring to the accompanying diagram, a suitable arrangement of apparatus in simplified form is illustrated for carrying out the process of this invention. Any suitable apparatus comprising a series of fixed catalyst sub-beds having a point for introducing an inlet stream or withdrawing an outlet stream between sub-beds, having a fluid-flow connecting path from one sub-bed to its next adjacent sub-bed, having fluid flow connecting means between the last sub-bed to the first sub-bed to serially interconnect the sub-beds of catalyst in a circular manner, and comprising a suitable means, such as a value or a manifold, for shifting the points of inlet and outlet of the inlet and outlet streams of the process may be provided. It is also within the scope of this invention that a single, vertical, continous bed of catalyst having vertically disposed multiple points to introduce inlet streams or withdraw outlet streams, having fluid flow connecting means between the bottom and the top of the catalyst bed to serially interconnect the catalyst bed in a circular manner, and comprising a suitable means, such as a valve or manifold, for shifting the points of inlet and outlet of the inlet and outlet streams of the process may be provided. In this description, the term catalyst "bed" refers to the entire amount of catalyst loaded in the reactor, however, the bed may be divided into smaller units of essentially equivalent catalyst volume which are herein designated as "sub-beds". The accompanying diagram illustrates a preferred apparatus design, being particularly suitable because of its compact arrangement of the series of fixed sub-beds in adjacent, superadjacent and subadjacent relationship to each other. The series of fixed sub-beds, such as sub-beds 1'–4–, may be a number of horizontally spaced, separate beds interconnected by a pipe from the bottom of one sub-bed to the top of its downstream adjacent sub-bed, or the sub-beds may be stacked one upon another, within a suitable vertical column, as illustrated in the accompanying diagram. The sub-beds herein are placed in their entirety in reactor 1, which contains suitably shaped partitioning means to divide the vertical column into a series of adjacent sub-beds, each sub-bed being divided from its adjacent sub-bed by a funnel-shaped partitioning member such as partition 2 in sub-bed 1', having a downcomer 3 of restricted cross-sectional area in open communication with an outlet nozzle 7 and opening into a subadjacent sub-bed 2' through a transverse partitioning member 4 which comprises the upper boundary of said adjacent sub-bed 2'. Other partitioning means such as those described in U.S. Pat. Nos. 3,208,833 and 3,214,247 are also suitable.

The advantages of constricting the width of the bed at the entry and withdrawal points of the various streams are: (1) prevention of convective back-mixing of fluid in a direction opposite to the direction of fluid flow and, (2) greater ease of distributing fluids flowing into and out of the reactor because of the ability to thereby eliminate channeling and other undesirable loss of uniform distribution.

The process of which the accompanying diagram is directed is described by reference to a particular arrangement of multiple beds of fixed or stationary solid catalyst and to a process operated under essentially liquid phase conditions, but it will be understood that other arrangements of beds, vapor or gaseous phase operation, and the use of other types of equipment are also contemplated within the broad scope of the present invention.

Although the solid catalyst is described as being distributed in a plurality of fixed beds, it is obvious that the series of interconnecting zones actually constitutes a continuous, vertical bed interconnected by conduits of reduced cross-sectional area. A fluid pump is provided between at least one pair of adjacent beds to provide a positive, unidirectional (downstream) flow of fluid. One of the essential characteristics of the process is that a continuously flowing stream of fluid (either liquid or vapor phase) is circulated through the series of beds from the first to the last in the series, to which stream, which is herein designated as the internal fluid, at least two inlet feed streams are introduced and at least one outlet product stream is withdrawn.

The terms "upstream" and "downstream" as used herein indicate points of reference relative to the flow of an internal fluid stream countercurrent to the apparent flow of the solid particles of catalyst, a point upstream designating a point in the continuous flow of fluid already passed and a point downstream designating a point in the stream of fluid yet to be contacted. Since the flow of hydrocarbons is countercurrent relative to the solid catalyst, a point downstream in the direction of fluid flow is, in effect, upstream in he simulated flow of catalyst, which is made to appear to flow by periodically moving the points of introduction of inlet streams and points of withdrawal of product streams in the same direction as the flow of internal fluid through the column. Although some minor variation is allowable, the change in location of all inlet and outlet streams occurs essentially simultaneously and the shift in location of each inlet and outlet stream is in a downstream direction essentially an equal distance. A simulated moving catalyst bed effect is thus achieved, and the effect becomes cyclic as the points of inlets and outlets advance in a downstream direction until the original reference point is reached, ending a given cycle. Accordingly, the present process is herein characterized as a "cyclic" and "continuous" process. It is thereby intended to define a method in which the various feed and product streams are charged into and withdrawn from the system in a continuous manner, without interruption, with respect to either the flow rate or composition of the several streams, and the points of introduction of inlet streams and the points of withdrawal of product streams are advanced in a downstream direction with regard to the internal fluid flow within the system. Although the solid catalyst remains in fixed position, a simulated countercurrent flow arrangement is thereby established, since incoming feed is contacted at its point of introduction with catalyst relatively fresh in comparison with downstream contacting zones.

For the purpose of this description, the boundary of a "zone" is defined by successive fluid inlet streams into and outlet streams from the catalyst bed. A zone will always be in the same relative position in relation to inlet and outlet streams, and may contain catalyst, void space, partitions, distributors, and other equipment. A typical arrangement of the several zones comprising the present process for the operation of a continuous, simulated countercurrent flow, fixed bed process at a given instant of the process cycle is illustrated in the accompanying diagram, a reactant mixture being introduced into the farthest upstream point of the so-called "reaction zone" (zone I) of the process, the reaction zone being relatively upstream with respect to a "buffer zone" (zone II), from which a product stream is withdrawn, the latter being upstream with respect to a "reactivation zone" (zone III) into which a reactivation stream is introduced, and the reactivation zone being upstream with respect to a secondary buffer zone (zone IV) from which a second product stream is withdrawn. Because of the cyclic flow of fluid within the process, the secondary buffer zone is also upstream with respect to the aforementioned first zone in series, that is, the reaction zone.

It is to be noted that the stage of the cycle illustrated is shown for illustrative purposes only to indicate the relationship of the various feed and product streams and the flows of the various streams in the particular instant that the zones occupy the positions shown. In the illustration, the reaction zone occupies sub-bed 1', the buffer zone occupies sub-bed 2', the reactivation zone occupies sub-bed 3', and the secondary buffer zone occupies sub-bed 4'; at a subsequent stage of the cycle, for example, after the first downstream shift of the points of introduction of the inlet streams and the points of product streams withdrawal, the reaction zone occupies the portion of catalyst bed previously comprising the buffer zone, the latter zone occupies the portion of catalyst bed formerly comprising the reactivation zone, the reactivation zone occupies the portion of catalyst bed formerly comprising the secondary buffer zone, and the latter zone occupies the portion of catalyst bed formerly comprising the reaction zone.

In the stage of the cycle illustrated, reactants enter the pump around line 5 via line 6 and are introduced into the top of sub-bed 1', a product stream is withdrawn via line 7 at a locus at the top of sub-bed 2', a reactivation stream is introduced into the top of sub-bed 3' via line 8 and a second product stream is withdrawn via line 9 at a locus at the top of sub-bed 4'. In order to maintain the present process on a continously cyclic basis, fluid removed from the bottom of sub-bed 4' is pumped into the top of sub-bed 1'. This stream is referred to as pump around fluid and continuously varies in composition and flow rate, depending upon the function of the bottom catalyst sub-bed in the particular stage of the cyclic operation. From the bottom of sub-bed 4', a pump around fluid is withdrawn via line 5, and is pumped via pump around pump 10 at the top of the reactor 1 where it enters sub-bed 1' together with the reactants stream. The flow rates of the inlet, outlet, and pump around streams are controlled by the corresponding valves 11, 12, 13, 14, and 15. After a suitable period of operation, the points of introduction or withdrawal of the reactants, product, and reactivation streams are advanced to the next downstream points of inlet or outlet, i.e., the reactants stream is introduced into reactor 1 via line 7, the product stream is withdrawn via line 8, the reactivation stream is introduced via line 9, and the second product stream is withdrawn via line 6. After a second suitable period of operation, the streams are advanced again to the next downstream point of inlet or outlet, and after a third and a forth suitable period of operation and a third and a fourth advancement of the streams, the streams will be in their reference positions shown in the accompanying diagram, and a full cycle will be complete.

An important part of the present invention, important that is, to the realization of the type of flow provided by the present method of operation is the provision of a suitable programming device for changing the points of inlet and outlet into and from the reactor and for advancing these in a downstream direction during the operation of the process. Any suitable form of fluid distribution center, such as a manifold arrangement of values and incoming and outgoing lines may be provided with timed, electrically operated switches to open and close the appropriate valves in a periodic fashion. The change in positions may be simultaneous or non-simultaneous depending on the program and valve system employed. The programming principle may also be suitably effected by means of a rotary plug valve of particular design as illustrated in U.S. Pat. No. 2,985,589 and others, however, the specific means for changing the inlet into and outlet from the reactor zones, and advancing the points of introduction of inlet streams and the points of withdrawal of product streams is not essential to the present invention.

In the present description, the reactor, catalyst inlet and outlet points, etc., are referred to in their entirety as the "reactor system". Referring to the attached drawing, a reactant stream is introduced into the reactor system, admixes wih the internal fluid, and is introduced into the first sub-bed of the reaction zone. Depending on the rate of reaction, volume of catalyst present in each sub-bed, and operating conditions, one or more sub-beds, up to about 20 are required in the reaction zone to carry out the reaction to the desired completeness. In the reaction zone, a polymeric material, coke, adsorbed reactant, adsorbed reaction product etc., adheres to the catalyst and is maintained in adherence with the catalyst as the zones pass through the catalyst bed, i.e., as the catalyst flows in simulated motion countercurrent to the internal fluid flow. The material adhering to the catalyst is swept into the secondary buffer zone together with a portion of the non-adhering components of the internal fluid as a result of the advancement of inlet and outlet streams. Referring to the attached drawing, catalyst sub-bed 1' is the reaction zone at the instant illustrated. The instant following advancement of the inlet and outlet streams, the internal fluid occupying the former reaction zone will be in the secondary buffer zone (zone IV). In zone IV, the material adhering to the catalyst continues to do so, but the non-adhering material is swept back into the reaction zone by force of the internal fluid flow through zone IV. Accordingly, there is a composition gradient of the non-adhering material in a downstream direction through zone IV, which contains a sufficient number of catalyst sub-beds to provide the desired content of the non-adhering material at the top of the first (farthest upstream) sub-bed of zone IV. About 1 to 20 catalyst sub-beds are needed in zone IV. It is also evident that reaction is initiated in zone IV, as reactant is introduced into zone IV by advancement of the inlet and outlet streams. At the bottom of the last (farthest downstream) sub-bed of the reaction zone, a portion of the internal fluid is withdrawn as a procuct stream and passed to a suitable separation zone wherein the components are separated as desired. The internal fluid at the downstream end of the reaction zone includes reaction products and unreacted reactants; the portion not withdrawn in the product stream passes into the buffer zone (zone II). Depending on the operating conditions of zone II, it may be utilized to either prevent or allow passage of reaction products and unreacted reactant components into the reactivation zone (zone III). In the former case, which is designated as "negative flow", relatively more catalyst sub-beds are required than in the latter case, but in both cases, about 1 to 20 sub-beds are required. Reaction products and unreacts reactants are prevented from passage into zone III by suitable control of the flow rate of internal fluid in zone II in relation to the void volume between catalyst particles and the frequency of advancement of inlet and outlet points of the reactor system. An advancement rate may be determined by dividing the void volume between catalyst particles of a zone by the time interval of advancement of the inlet/outlet point from the upstream side to the downstream side of that zone. When the advancement rate is greater than the internal fluid rate of zone II, the effect is a simulated co-current flow of catalyst and fluid in zone II; i.e., reactivation medium is withdrawn as part of the product stream because the points of inlet/outlet are advanced faster than the catalyst void volume is swept of reactivation medium. When the advancement rate is slower than the internal fluid rate of zone II, reaction products and unreacted reactants pass through zone II and enter zone III, in which case flow is designated as "positive". When the rates are equal, a simulated plug or "balanced" flow is effected to maintain separate the components of zones I and III. By the same mechanism, it is possible to control flow in zone IV to achieve either positive or negative flow. At the downstream boundary of zone II, a reactivation medium is introduced into the system to reactivate the catalyst in zone III, i.e., to remove from the catalyst particles the material adhering to and deactivating the catalyst as described hereinabove. About 1 to 20 sub-beds of catalyst are required to effect the desired catalyst reactivation. Downstream of the reactivation zone, a second product stream including reactivation medium and the material adhering to the catalyst is withdrawn to suitable separation.

While it is taught hereinabove that a deactivating agent is formed in the reaction zone and adheres to the catalyst therein, later to be removed from the catalyst in the reactivation zone, in another application of the inventive process a catalytic activator component normally adsorbed on the catalyst surface such as a chloride or water is removed from the catalyst by contact of the reactants stream and the internal fluid stream with the catalyst. The catalytic activator is withdrawn from the reaction system in a product stream, thereby resulting in depletion of the catalytic activator on the catalyst. To maintain a satisfactory level of catalytic activator and therefore a satisfactory level of catalyst activity, catalytic activator is introduced into the reaction system in the reactivation stream and is contacted with the catalyst in the reactivation zone, wherein the catalyst adsorbs sufficient catalytic activator to achieve a predetermined level.

Because a specific application of the present process may require little or no separation of the fluid components of the reaction and reactivation zones, i.e., the fluid components of the reaction and reactivation zones are intermixable without degradation of either products or catalyst, only a single product outlet stream may be provided, located immediately downstream of either the reaction or reactivation zone. In this case, the process comprises a reaction zone, a reactivation zone, and a single buffer zone. Especially preferred is a 3 zone process comprising a series a reaction zone followed by the reactivation zone followed by a buffer zone, and because of the cyclic nature of the process, followed by the reaction zone. Similarly a 3 zone process comprising a reaction zone followed by a buffer zone followed by a reactivation zone is within the scope of the present invention. Flow in the buffer zone of a 3 zone process may be either positive, negative, or balanced. In an embodiment wherein flow through the buffer zone is positive, fluid components of the reaction and reactivation zones are intermixed whereas in an embodiment wherein negative flow is effected in the buffer zone, fluid components of the reaction zone or the reactivation zone, whichever is immediately downstream of the buffer zone, pass into the third zone, but the components of the zone upstream of the buffer zone do not pass into the zone downstream of the buffer zone.

The present inventive process requires as a minimum two inlet streams including a reactant stream and a reactivation stream, and one outlet product stream. Therefore, by the present definition of a zone as being bounded by successive inlet and outlet streams, the minimum number of zones is three. One skilled in the art will recognize the desirability of adding inlets or outlets to allow passage into or out of the reactor of additional streams. For example, but not as a limitation, reactant and reactivation streams may be introduced into the reactor system in multiple downstream injection points, inert purge streams may be introduced into a buffer zone, etc. Each additional inlet or outlet greater than the minimum of three will result in an additional zone in the reactor. In a specific application of the process, 3, 4, 5 or more zones may be desirable.

Each zone of the reactor may contain a portion of a single bed of catalyst, or, in a preferred mode of operation, each zone may contain a plurality of 1 to 20 sub-beds, each sub-bed having an identical configuration and an essentially equivalent quantity of catalyst. The advantage of providing a plurality of catalyst sub-beds within a zone as compared with a single catalyst bed within a zone lies in the resulting increase in continuity in the process in the respect that the composition of the internal fluid stream at any point within a zone is maintained within a narrower range of fluctuation as the number of catalyst sub-beds increases while the catalyst content within a zone remains constant. However, increasing the number of sub-beds requires greater capital investment. Each sub-bed is bounded by a point to allow introduction of a reactivation stream or reactants stream, or withdrawal of a product stream. In the simplest embodiment, such a point for introduction of an inlet stream or withdrawal of a product stream comprises a nozzle welded to the reactor shell and drilled out to provide open communication through the nozzle to the fluid flowing within the reactor. In a preferred arrangement, each sub-bed is separated from its adjacent sub-bed by fluid collection means described hereinabove.

With zones of a reactor configuration as shown in the attached drawings, i.e., in adjacent, superadjacent, and subadjacent relationship to each other, it is a requirement of the present invention to pass the fluid removed from the bottom of the bottommost zone to the top of the uppermost zone. This is done by means of a pump when the fluid is liquid, or a compressor when the fluid is gaseous, the fluid stream being referred to as a pump-around stream and allowing the process to operate on a cyclical basis. Adjustment of the pump around rate must be made in accordance with a desired flow rate through a specified zone of the reactor, and will determine an internal fluid flow rate in the reactor, this internal flow rate being a different rate in each zone as inlet and outlet streams are introduced into and withdrawn from each zone.

While the illustration in the attached drawing shows the countercurrent flow pattern with catalyst moving in a simulated upward direction and fluid flowing through the catalyst bed in a downward direction, and the advancement of inlet and outlet streams in a downward direction, a countercurrent flow in an opposite direction may also be achieved by withdrawing fluid to the pump around circuit from the top of the reactor and passing it into the bottom of the reactor, thereby creating an upward fluid flow in the reactor, and advancing the position of the inlet and outlet streams in a downstream direction which will now be in an upwardly direction.

The process of this invention is operated at conditions of temperature, pressure, catalyst space velocity, and other process conditions which depend upon the particular feed stock, catalyst, and required product purity. In general, in liquid phase operations the pressure is substantially less than when employing a gaseous phase condition, the latter generally being dependent upon the molecular weight of the reactants. In an application of the present invention to flue gas desulfurization, for example, the pressure may be 1 to 5 atmospheres whereas in hydrodesulfurization, the pressure of the process may be 40 to 200 atmospheres or more.

Process temperatures also vary substantially, from about 0° C. to 700° C. Reactant and reactivation streams may be introduced into the process at substantially different temperatures resulting in different temperature levels from one zone to another zone of the process. Heat may be added or withdrawn from a zone by withdrawing a stream from a zone, heating the stream or cooling it by indirect heating or cooling means known in the art, and returning the stream to the zone, but for economy of energy, it is desirable to heat or cool the process only by inlet streams introduced into the process.

The fluid flow rate in a reactor of the present process is adjusted to provide a charging rate consistent with maintenance of fixed bed conditions, which is dependent upon whether gas phase or liquid phase contacting is utilized, the size of the particles of catalyst, the degree of packing of catalyst in the confines of the bed, and the direction of flow. When utilizing gaseous feed stocks and displacing agents, the fluid flow rate in the reactor is below the rate at which fluidization of the catalyst particles occurs, at a rate preferably not in excess of about 3000 volumes/hour of internal fluid per volume of catalyst, more desirable at a rate of from about 0.06 to 600 volumes/hour of internal fluid per volume of catalyst. When utilizing liquid phase contacting conditions, fluid flow rate is desirably not greater than about 50 volumes/hour of feed per volume of catalyst and more desirably from about 0.01 to about 30 volumes/hour of feed per volume of catalyst when utilizing relatively large granular particles of catalyst. These rates are, of course, dependent upon the size of the catalyst particles, the depth and width of the beds, specific processing conditions, and mechanical design of the apparatus. When catalyst completely fills the reactor, the limiting rate of flow of fluid through each bed is set by the free or "void" space between particles of catalyst, the space thus provided establishing a maximum accommodation flow for any given pressure differential, but which may be increased if a greater pressure differential is tolerable. The finer the particles of catalyst, the greater the pressure drop through each bed, resulting in an ultimate permissible flow rate being fixed as the rate which does not give rise to a pressure drop through all of the beds greater than the discharge pressure delivered by the circulating fluid pump.

Advancement of the inlet and outlet streams of the present invention is made from one point to the next successive point for introducing or withdrawing a stream, the time interval between advancement from one point to the next successive point being referred to as an advancement speed. In a cycle, each inlet stream is introduced and each product stream is withdrawn through each inlet/outlet point provided, and is advanced in a timed sequence at a predetermined cycle rate, i.e., the time required to complete one cycle. The cycle rate is about 5 minutes to 24 hours, with a preferred cycle rate of about 5 minutes to 3 hours. For example, in a reactor system comprising 20 catalyst sub-beds, 20 points are provided to introduce or withdraw a stream; a cycle rate of 60 minutes results in advancement of the inlet/outlet streams every 3 minutes. The advancement speed may vary slightly from one sub-bed to another, but it is preferred that the advancement speed be equal for all sub-beds.

PREFERRED EMBODIMENTS

The process of the present invention may be applied to the alkylation of isobutane, isopentane or similar alkylatable isoparaffins. The preferred isoparaffins are isobutane and isopentane, particularly isobutane. A mixture of two or more isoparaffins may also be employed, if desired. Conventional isobutane alkylation feed stocks are suitable for use in the present process. Such conventional makeup isobutane feed stocks may contain some non-reactive hydrocarbons such as normal paraffins. For example, a conventional commercial isobutane alkylation feed stock generally contains about 95 weight percent isobutane, 4 weight percent n-butane and 1 weight percent propane. Monoolefins which are suitable for use in the process of the present invention with the alkylatable isoparaffins stated above include $C_2$–$C_5$ olefins. Mixtures of two or more olefin compounds may also be employed in the present process with good results. For example, conventional olefin feed stocks used in commercial olefin alkylation operations contain mixtures of propylene and butylenes, butylenes and amylenes, or propylene, butylenes and amylenes. The benefits of the present process may be obtained using such feed stocks as well as when using a single olefin. A $C_2$–$C_5$ olefin alkylation feed stock, which is particularly preferred for use in this process, may be derived from petroleum refining operations such as catalytic cracking and may therefore contain substantial amounts of saturated hydrocarbons, lighter and heavier olefins, etc.

Alkylation of isoparaffinic hydrocarbons, such as isobutane, iosopentane, and the like, with olefinic hydrocarbons such as propylene, butylenes, amylenes, and olefin-acting compounds such as $C_2$–$C_5$ alkyl halides, etc., is well known as a commercially important method for producing gasoline boiling range hydrocarbons. The $C_5$–$C_{10}$ hydrocarbons typically produced by the isoparaffin-olefin alkylation reaction are termed "alkylate". Alkylate is particularly useful as a motor fuel blending stock because of its high motor and research octane ratings, such that it can be used to improve the overall octane rating of gasoline pools to comply with the requirements of modern automobile motors. These high octane alkylate fuel components are particularly important in producing motor fuels of sufficient quality when it is desired not to employ alkyl lead compounds in the fuel to meet octane requirements.

The process of the present invention may also be applied to the alkylation of an alkylatable aromatic such as benzene, toluene, ethylbenzene, or cumene, a preferred alkylatable aromatic being benzene. Monoolefins which are suitable for use in the present process with alkylatable aromatics such as those stated above include $C_9$–$C_{15}$ mono-olefins, the result of alkylation of these reactants being a $C_9$–$C_{15}$ side chain alkylaromatic hydrocarbon which is useful in the manufacture of detergents.

Another application of the present process is the alkylation of benzene with ethylene to form ethylbenzene.

Still another application of the present process is the alkylation of benzene with propylene to form isopropylbenzene (cumene).

In a preferred embodiment of the invention, a simulated moving bed reactor system is applied to an alkylation reaction of an olefin-acting reactant with an alkylatable hydrocarbon to produce an alkylate product. A reactor system containing four vertical, adjacent zones of a solid, sorbent-acting, crystalline aluminosilicate zeolite catalyst is provided with internal fluid flow in a downward direction through said zones. A simulated catalyst movement in an upward direction is effected. Into the upstream end of a reaction zone, a reactant stream including principally olefin-acting reactant and paraffins is introduced together with an alkylatable hydrocarbon-rich internal fluid flowing from an adjacent secondary buffer zone, this fluid being the pump around fluid whenever the reaction zones is in an uppermost position in the reactor. Downstream of the reaction zone, a first product stream including principally paraffin and alkylatable hydrocarbon is withdrawn to a fractionation zone, said first product stream forming the downstream boundary of the reaction zone and the upstream boundary of an adjacent primary buffer zone. In the former zone, a reaction and partial separation of reactants takes place as the olefin-acting reactant and alkylate product are more strongly absorbed in the pores of the catalyst than the paraffins and alkylatable hydrocarbon, and during a subsequent part of a cycle are carried into the secondary buffer zone upstream of the reaction zone. In the primary buffer zone (zone II), paraffin concentration decreases in a downstream direction as a result of suitable adjustment of the internal fluid flow rate through zone II to be less than or equal to the rate of advancement of the inlet and outlet streams into and out of the reactor system when the rate of advancement is expressed as the rate of flow of catalyst void volume, i.e., the volume between particles of catalyst, as described hereinabove. The internal fluid stream flowing downstream through the primary buffer zone of the process is admixed at the downstream boundary of that zone and the upstream boundary of an adjacent reactivation zone with an inlet stream of reactivation medium including principally alkylatable hydrocarbon. In this preferred embodiment, the reactivation stream acts as a desorbent in the reactivation zone and provides alkylatable hydrocarbon in sufficient quantity that it is maintained throughout the reactor system as the principal component of the internal fluid stream. As desorbent, it is capable of displacing from the solid sorbent-acting catalyst the component sorbed in the catalyst pores during the part of the cycle when the catalyst was present in the reaction zone, thereby reactivating the catalyst. The displacing action is primarily a mass action effect and requires a molar ratio of desorbent to sorbate of about 1/1 to 100/1. As the internal fluid passes downstream through the reactivation zone, it becomes enriched in alkylate and unreacted olefin-acting reactant, the alkylatable hydrocarbon displacing alkylate and olefin-acting reactant from the sorbent-acting catalyst and taking the place of alkylate and olefin-acting reactant in the pores of the catalyst. At the downstream boundary of the reactivation zone, which is also the upstream boundary of an adjacent secondary buffer zone, a second product stream including principally alkylatable hydrocarbon, alkylate product, and unreacted olefin-acting reactant is withdrawn to the fractionation zone, wherein alkylate product is separated and recovered. Olefin-acting reactant concentration in the secondary buffer zone increases in a downstream direction, and with alkylatable hydrocarbon available in the internal fluid stream, reaction begins to take place in that zone, reaching the highest degree of reactivity at the point of introduction of the olefin-containing reactant stream. Operating conditions in the reactor include liquid phase operation, with sufficient pressure of about 10 to 30 atmospheres to obtain liquid phase operation, an external flow ratio of alkylatable hydrocarbon/olefin-acting reactant (alkylatable hydrocarbon in reactivation stream vs. olefin-acting reactant in reactant stream) of about 1/1 to 100/1 by volume, an internal flow ratio of alkylatable hydrocarbon to olefin-acting reactant calculated at the point of introduction of olefin-acting reactant of about 1/1 to 100/1 by volume, and temperature in the reaction and reactivation zones of about 100° to 400° F., preferably 150° to 250° F. A complete cycle time of about 10 minutes to 6 hours is preferred. Each zone contains 1 to 20 sub-beds of catalyst, which is in the form of particles of 2–20 mesh size, the total catalyst bed having a liquid hourly space velocity (volume per hour of olefin reactant/volume of catalyst inventory) of about 0.01 to 10.

A second preferred embodiment of the present invention is similar to the first in using a similar reactor system of four zones to perform an alkylation reaction in which a reactant stream containing principally olefin-acting reactant and paraffins is introduced into the upstream part of a reaction zone and a reactivation stream containing alkylatable hydrocarbon is introduced into the upstream part of a reactivation zone. As in the first preferred embodiment, alkylatable hydrocarbon is maintained as the principal component of the internal fluid stream. In the present embodiment of the inventive process the reactant stream is introduced at a temperature of about 100° F. to 400° F. and the reactivation stream is introduced at a temperature 10° F. to 150° F. hotter than the reactant stream. Catalysts suitable for the present embodiment are known in the art and, without limiting the embodiment to the catalysts listed, include solid phosphoric acid, crystalline aluminosilicate, halogenated alumina composited with platinum or palladium, a Friedel-Crafts type catalyst such as aluminum chloride on a solid support, mordenite composited with a metal component selected from copper, silver, and zirconium, and a boron trifluoride-modified refractory inorganic oxide. The catalyst utilized does not adsorb alkylate, and accordingly, the first product stream, located at the downstream boundary of the reaction zone and upstream boundary of the first buffer zone, includes alkylatable hydrocarbon, paraffins, and alkylate product. In the present embodiment, a solid polymer-like substance of higher molecular weight than alkylate product is formed as a by-product of the alkylation reaction in zone I and adheres to the catalyst surface thereby plugging the pores of the catalyst and deactivating it. The catalyst and heavy polymer pass in simulated flow from zone I into zone IV. As a result of shifting inlet and outlet points, at least a portion of the internal fluid present in the reaction zone is passed into zone IV but is returned to zone I by maintenance of a sufficiently high internal fluid flow rate in zone IV. At the upstream boundary of the reactivation zone (zone III) an alkylatable hydrocarbon-rich reactivation stream is introduced into the system to reactivate the catalyst by a washing effect, removing the heavy polymer at a higher temperature in the reactivation zone compared with the reaction zone. At the downstream boundary of the reactivation zone, a second product stream including alkylatable hydrocarbon and heavy polymer is withdrawn. Both product streams are passed to suitable fractionation to recover the alkylate product. Reactivated catalyst passes in simulated flow into zone II wherein at least a portion of the internal fluid is removed from the zone, indirectly cooled by suitable cooling means known in the art, such as a water cooled exchanger, to a temperature of about 50° F. to 200° F. and reintroduced into zone II for the purpose of cooling the catalyst in zone II in preparation for its utilization in zone I. The portion of internal fluid is preferably withdrawn from a restricted flow area described hereinabove between two sub-beds of zone II, is passed by pumping means to the cooling means, and is reintroduced into zone II and admixed with the internal fluid at a point either upstream of or downstream of the point of withdrawal, preferably at a point between two upstream catalyst sub-beds.

In a third preferred embodiment of the present inventive process, a three zone system is utilized to effect an alkylation reaction of an olefin-acting reactant with an alkylatable hydrocarbon to form an alkylate product. Catalyst utilized is selected from those listed in the second preferred embodiment described hereinabove. As an illustration of an alkylation reaction, reactants and catalyst suitable for the present embodiment, the alkylation of benzene with propylene over a solid phosphoric acid catalyst is described hereinbelow. The solid phosphoric acid catalyst utilized in the embodiment is well known in the art and may be made by mixing an acid of phosphorous, such as ortho-, pyro-, or tetra-phosphoric acid and a finely divided, generally siliceous, solid carrier (such as diatomaceous earth, prepared forms of silica, reactivated clays, and the like) to form a wet paste. The paste is then calcined at temperatures generally below about 500° C. to produce a solid cake which is thereafter ground and sized to produce particles of usable mesh. If the calcination is carried out at temperatures above about 400° C., it may be desirable to rehydrate the catalyst granules at a temperature between about 200° C. and 350° C., typically 260° C., to produce an acid composition corresponding to high alkylating activity. The catalyst preparation procedure may be varied by forming particles of the original paste by extrusion or by pelleting methods after which the formed particles are calcined, and, if necessary, rehydrated. A solid phosphoric acid catalyst prepared from a major portion by weight of a phosphoric acid having at least as large a water content as that of the pyro-acid and a minor proportion of the siliceous carrier, such as kieselguhr, is preferred for use in the present process. A preferred alkylation catalyst includes about 50 to 90 percent by weight phosphoric acid. The reaction system of the present embodiment includes a reactivation zone, a reaction zone, and a buffer zone in series in the order described, the last zone followed by the reactivation zone because of the cyclic nature of the process. Fluid flow is in a downward direction. Catalyst is loaded into the reactor system to provide each zone with 1 to 20 sub-beds. For example, the regeneration zone may comprise 15 sub-beds of catalyst, the reaction zone may comprise 10 sub-beds of catalyst, and the buffer zone may comprise 5 sub-beds of catalyst. Each sub-bed contains an equivalent quantity of catalyst which is sufficient to result in a liquid hourly space velocity of about 1 to 20 hour$^{-1}$ for each sub-bed when the catalyst quantity of each sub-bed is related to the summation of reactivation stream flow rate and reactant stream flow rate. A reactivation stream including principally benzene is introduced immediately upstream of the reactivation zone to reactivate the catalyst by a washing mechanism. In the alkylation reaction, it is presumed that oligomerization of the olefin reactant results in a polymeric substance of higher molecular weight than the alkylate product, this polymer depositing on the catalyst to occlude the active catalytic sites. Washing of thus deactivated catalyst with a hydrocarbon stream such as an aromatic stream and particularly a benzene stream removes at least a portion of the polymer deposit and reactivates the catalyst. Benzene introduced into the reactor system in the reactivation stream also serves to provide benzene reactant for the alkylation reaction as benzene is the principal component of the internal fluid and is maintained as a continuous component in the internal fluid. Internal fluid including principally benzene and also including polymeric material washed from the catalyst passes into the reaction zone in admixture with a reactant stream including propylene which is introduced between the reactivation and reaction zones. In the reaction zone, benzene and propylene react to form cumene. Downstream of the reaction zone, a product stream including benzene, cumene, unreacted propylene and polymer is withdrawn to suitable fractionation to recover the cumene product. Internal fluid passes into the buffer zone, which may be maintained with positive or negative flow, although negative flow is preferred in the present embodiment to thereby prevent flow of cumene, unreacted propylene, and polymer into the reactivation zone. In this embodiment, the inlet streams are introduced into the reaction system at a temperature of about 200° to 600° F. in liquid phase, and the pressure of the system is maintained at about 20 to 40 atmospheres to maintain the internal fluid in liquid phase. A cycle time of about 10 minutes to 5 hours is preferred. Benzene is introduced into the reaction system in sufficient quantity to achieve a benzene/propylene molar ratio at the upstream inlet point of the reaction zone of about 2/1 to 100/1. Because of the high molar excess of benzene introduced, as compared with the reaction requirements, benzene is maintained as a continuous component of the internal fluid.

We claim as our invention:

1. A continuous fixed bed catalytic alkylation reaction and catalyst reactivation process comprising the steps of:
   a. providing a fixed bed of solid catalyst containing four zones having a fluid flow connecting path between said zones to interconnect said zones;
   b. arranging said zones in a series and providing fluid flow connecting means between the last zone and the first zone of the series to provide a directional circular flow path through said zones;
   c. providing a point between each two successive zones for introducing an inlet stream or withdrawing a product stream;
   d. introducing a reactivation stream including alkylatable hydrocarbon at a first point located between two successive zones (zone II and zone III) to effect catalyst reactivation and to provide alkylatable hydrocarbon as a continuous component throughout said fixed bed of solid catalyst;
   e. simultaneously withdrawing a first product stream from a second point located between said zone III and the next successive zone in the direction of flow (zone IV);
   f. simultaneously introducing reactants consisting essentially of isobutane, isopentane or a mixture thereof and at least one $C_2 - C_5$ olefin into said fixed bed of catalyst at a third point located between said zone IV and the next successive zone in the direction of flow (zone I) and reacting said reactants at a temperature of about 100° F to 400° F to effect an alkylation reaction, a result of which is deactivation of said catalyst, said alkylation and catalyst reactivation being the principal reactions of the process;
   g. simultaneously withdrawing a second product stream from a fourth point located between said zone I and the next successive zone in the direction of flow (zone II); and,
   h. periodically advancing downstream the points of charging said reactants and said reactivation stream, and the points of withdrawal of said product streams to the next successive points for introducing an inlet stream or withdrawing an outlet stream.

2. The process of claim 1 further characterized in that each of said zones contains 1 to 20 sub-beds of catalyst in series, each sub-bed having a fluid flow connecting path to connect said sub-bed with the previous and successive sub-bed in the series, and there being a point provided between each two sub-beds for introducing an inlet stream or withdrawing a product stream.

3. The process of claim 1 further characterized in that the points of charging said reactants stream and said reactivation stream and the points of withdrawing said product streams are periodically advanced downstream a substantially equal distance.

4. The process of claim 1 wherein said catalyst is a crystalline aluminosilicate zeolite.

5. A continuous fixed bed catalytic alkylation reaction and catalyst reactivation process comprising the steps of:
   a. providing a fixed bed of solid catalyst containing three zones having a fluid flow connecting path between said zones to interconnect said zones;
   b. arranging said zones in a series and providing fluid flow connecting means between the last zone and the first zone of the series to provide a directional circular flow path through said zones;
   c. providing a point between each two successive zones for introducing an inlet stream or withdrawing a product stream;
   d. introducing a reactivation stream including alkylatable hydrocarbon at a first point located between two successive zones to effect catalyst reactivation and to provide alkylatable hydrocarbon as a continuous component throughout said fixed bed of solid catalyst;
   e. simultaneously withdrawing a first product stream from a second point located between another two successive zones;
   f. simultaneously introducing reactants consisting essentially of a isobutane, isopentane or a mixture thereof and at least one $C_2 - C_5$ olefin into said fixed bed of catalyst at a third point located between the remaining two successive zones and reacting said reactants at a temperature of about 100° to 400° F to effect an alkylation reaction, a result of which is deactivation of said solid catalyst, said aromatic alkylation and catalyst deactivation being the principal reactions of the process; and, g. periodically advancing downstream the points of charging said reactants stream and said reactivation stream, and the point of withdrawal of said product stream to the next successive points for introducing an inlet stream or withdrawing an outlet stream.

6. The process of claim 5 further characterized in that each of said zones contains 1 to 20 sub-beds of catalyst in series, each sub-bed having a fluid flow connecting path to connect said sub-bed with the previous and successive sub-bed in the series, and there being a point provided between each two sub-beds for introducing an inlet stream or withdrawing an outlet stream.

7. The process of claim 5 further characterized in that the points of charging said reactants stream and said reactivation stream and the point of withdrawing said product stream are periodically advanced downstream a substantially equal distance.

8. The process of claim 5 wherein said catalyst is a crystalline aluminosilicate zeolite.

9. The process of claim 5 further characterized in that said three points are located in successive order in a downstream direction as follows: first point, second point, and third point; and because of the cyclic nature of the process, said third point is followed by said first point.

10. The process of claim 5 further characterized in that said three points are located in successive order in a downstream direction as follows: first point, third point, and second point; and because of the cyclic nature of the process, said second point is followed by said first point.

* * * * *